(12) United States Patent
DeRoos et al.

(10) Patent No.: US 6,482,433 B1
(45) Date of Patent: Nov. 19, 2002

(54) ENCAPSULATION OF ACTIVE INGREDIENTS

(75) Inventors: Kris Bart DeRoos, Wetzikon (CH); Matthias Perren, Brugg (CH); Gregory Alan Sherman, Cincinnati, OH (US)

(73) Assignee: Givaudan SA (CH)

( * ) Notice: Subject to any disclaimer, the term of this patent is extended or adjusted under 35 U.S.C. 154(b) by 0 days.

(21) Appl. No.: 09/606,518

(22) Filed: Jun. 29, 2000

(30) Foreign Application Priority Data

Jun. 30, 1999 (EP) .............................. 99112446

(51) Int. Cl.⁷ .............................. A61K 9/14; A61K 9/20
(52) U.S. Cl. ........................ 424/464; 424/439; 424/484; 424/485; 424/488; 424/489; 514/773; 514/777; 514/778; 514/782; 514/783; 514/951
(58) Field of Search ................................ 424/489, 464, 424/465, 488, 484, 485, 439

(56) References Cited

U.S. PATENT DOCUMENTS

| | | |
|---|---|---|
| 3,314,803 A | 4/1967 | Dame, Jr. |
| 3,554,768 A | 1/1971 | Feldman |
| 3,971,852 A | 7/1976 | Brenner |
| 4,532,145 A | 7/1985 | Saleeb |
| 4,576,737 A | 3/1986 | Johnson ...................... 252/522 |
| 4,634,598 A | 1/1987 | Liu et al. .................... 426/650 |
| 5,124,162 A | 6/1992 | Boskovic et al. |

FOREIGN PATENT DOCUMENTS

| | | | |
|---|---|---|---|
| EP | 0 861 852 A1 | 9/1998 | ........... C08B/37/18 |
| FR | 2686486 | 1/1992 | |
| WO | 91/17821 | 11/1991 | |

OTHER PUBLICATIONS

W.J. Coumans, P.J.A.M. Kerkhhof, and S. Bruin, Drying Technol. 12 (1 and 2), 99–149 (1994).

*Primary Examiner*—James M. Spear
(74) *Attorney, Agent, or Firm*—Wood, Herron & Evans, L.L.P.

(57) ABSTRACT

A process for preparing free-flowing and, during handling, dust-free microparticles. The particles are at least 90% by weight, have a diameter of 100–400 $\mu$m, and contain one or more active ingredients in a glassy matrix. Generally, the process of the invention comprises the steps of (1) preparing an aqueous solution of the matrix materials, (2) mixing the flavor into the aqueous solution with stirring to form an emulsion or suspension, (3) spraying the emulsion in a spray drying tower under a supply of hot air to quickly create a semi-solid skin allowing outtake of moisture (water), and (4) subsequently subjecting the resulting particles to continued drying at lower temperatures in a fluid bed.

40 Claims, No Drawings

ENCAPSULATION OF ACTIVE INGREDIENTS

This application claims priority to European Patent Application Serial No. 99112446.2 filed Jun. 30, 1999.

BACKGROUND

There exists a demand for encapsulating active ingredients, which are food, feed, beverage or pharmaceutical additives, especially vitamins and more specifically flavors. Among them, the need for dry versions of liquid flavors is important. Particularly, dry versions of liquid flavors are needed for flavoring dry food and beverage products such as, for example, tea, instant coffee, instant soups and desserts, dry beverage powders, effervescent tablets and pharmaceutical products.

Several techniques have been developed for producing dry flavors. Among them, the techniques of plating on a carrier and spray drying are most widely used. These methods are simple and cost saving. However, both techniques have the serious disadvantage of providing no protection or only limited protection of the flavor against heat, moisture, and oxidation. Hence the appropriate encapsulated flavors have poor shelf life stability. Therefore, these methods are not suitable for use in combination with flavors sensitive to oxidation such as, for example, citrus flavors.

In this respect, one of the most successful approaches to produce dry flavors, and especially to improve the shelf life stability of dry flavors, is their encapsulation in a glassy sugar matrix. The preferred technology for producing glassy encapsulated flavors is extrusion. Products of extrusion technology are very stable against oxidation and show high retention of volatiles during storage. However, extruded flavors are considerably more expensive than spray dried flavors because of the relatively low flavor load and the need of using a multi-step and multi-component process consisting of at least a heating, an extruding, a washing (usually with isopropanol), a drying and a grinding step. Moreover, a solvent recovery step normally has to be included as well. Another drawback of encapsulation of flavors by the extrusion technique is that the flavor is subjected to high temperatures, which might induce decomposition of sensitive flavor constituents. Hence, there exists a need to keep the melt temperature as low as possible, but this limits the choice of carrier materials. Low molecular weight carbohydrates, in combination with plasticizers such as glycerin and water, are used to keep the melt temperature as low as possible. However, a high content of low molecular weight carbohydrates and glycerin increases the hygroscopicity of the resulting powder which, in turn, results in a non-free-flowing, sticky product with a high risk of lump formation. Increase of water content is also problematic because of the enhanced flavor losses at the exit of the extruder and/or subsequent drying step.

U.S. Pat. No. 3,971,852 describes microparticulate compositions with flavor oil encapsulated in a glassy matrix that consists of a mixture of a polysaccharide with emulsifying properties and low molecular weight polyhydroxy compounds such as sugars or sugar alcohols. Standard spray drying is used to produce spherical particles having a flavor oil content of up to 80% by volume and an extractable oil of not more than 5%. The stability of the resulting dry flavors is claimed to be better than spray dried flavors prepared according to prior art methods.

U.S. Pat. No. 3,314,803 describes a method for encapsulating volatile flavor compounds in a glassy mannitol matrix by spray drying.

U.S. Pat. No. 3,554,768 describes a method for fixing acetaldehyde in selected carbohydrates by drying an aqueous solution of acetaldehyde and selected carbohydrates.

One of the drawbacks of the above mentioned methods is the high hygroscopicity of the matrix materials. To achieve good stability these products require storage under exclusion of ambient moisture and air. Thus, antioxidants have to be added to prevent oxidation of the flavors fixed in the matrix.

U.S. Pat. No. 4,532,145 describes a spray drying method for encapsulating volatile flavor compounds in a spray dried, moisture-stable matrix consisting of 10–30% low molecular weight carbohydrate such as maltose and at least 70% high molecular weight materials such as maltodextrin. Spray drying is carried out at relatively low temperature, i.e. the inlet temperature ranging from 100–180° C. and the outlet temperature ranging between 50–80° C.

U.S. Pat. No. 5,124,162 describes a method to prepare a moisture and oxygen stable, antioxidant free, fixed flavor having a free flow bulk density of at least 0.5 g/ml and a void space of less than 20% of the spray dried solids, comprising a flavorant encapsulated in a carbohydrate matrix consisting of 22–45% of mono- and disaccharides wherein at least 50% of the mono- and disaccharides is maltose, from 25–50% maltodextrin and from 10–35% high molecular weight film forming carbohydrate. The encapsulated flavor is said to be stable against oxidation for one year at 70° F. The products are obtained at moderate inlet and outlet temperatures of 100–180° C. and 70–100°C., respectively.

In all above mentioned spray drying techniques the thermoplastic nature of glassy matrices pose significant processing problems, especially sticking of the thermoplastic particles to the wall of the dryer. Moreover, loss of volatile flavor compounds is still substantial and the resulting powders have relatively small particle size, resulting in dust formation during handling.

With a multi-stage spray drying method, detrimental effects of particle expansion are avoided by spraying at high air temperature to create particles having a semi-solid surface in the form of a quickly built skin, and subsequent continued drying at lower air temperature in a fluid bed or moving belt dryer. The positive effect of two-stage spray drying on aroma retention has been confirmed experimentally by W. J. Coumans, P. J. A. M. Kerkhof and S. Bruin, Drying Technol. 12 (1 and 2), 99–149 (1994). According to the described process it is not possible to produce particles having high shelf life stability, i.e. having oxygen stability and/or low or no active ingredient diffusing out.

French Patent 2,686,486 discloses a method for drying honey using a multistage spray dryer. The advantage of this drying process is said to be the minimum decomposition of sensitive ingredients like vitamins and flavor compounds due to the low temperature during drying. No attempts have been reported to encapsulate flavors.

PCT publication WO 91/1782 discloses a method for preparing microcapsules encapsulating flavorants by multistage spray drying. An emulsion, a suspension or a solution of flavorant and matrix material is sprayed into a spraying tower in a cloud of simultaneously introduced fine particles of starch at 50–120° C. The emulsion drops, having freshly solidified surfaces, were then transferred to a fluidized bed and maintained fluidized for several hours at 30° C. The particles were more dense and larger than prior art microcapsules, contributing to reduced exposure to oxygen. But a drawback of this process is the long drying time in the fluid bed dryer and the need for introducing a second carrier or coating. The long resting time in the fluidized bed is necessary because the already solidified surface of the particles derived from spray drying hinder the water content inside the particles to migrate out easily, especially to diffuse out of the central part of the particles, thereby also losing sensitive fragrant materials.

From the above description of the prior art it results that there exists a need for a process which overcomes most of the aforementioned disadvantages or which at least improves an already known process.

SUMMARY

The invention is directed to a method for encapsulating an active ingredient in a matrix to form a free flowing particle that is dust free during handling. In the method, a suspension or emulsion of the active ingredient, such as a flavor, fragrance, or vitamin, is prepared in an aqueous solution of matrix material. The particles formed are dried, for example in a fluid bed or moving belt dryer, at an air temperature sufficient to render the matrix material permeable to water but impermeable to the active ingredient. The particles are further dried at an air temperature of about 25–55° C., lower than previously used, resulting in free-flowing dust free particles. The particles are heat-, oxygen-, and moisture-stable, contain about 1–30% by weight on a non-aqueous basis of the active ingredient, and have a size of 400 $\mu$m or lower.

The particle matrix is composed of at least one low molecular weight water soluble molecule such as a carbohydrate or polyhydroxy compound, and at least one high molecular weight film forming agent such as protein, gum acacia, pectin, modified starch, and/or a polyglycerol fatty acid ester.

In the method, particles below about 100 $\mu$m may be recycled to achieve the desired size. These particles may be recycled from a fluid bed dryer into a spray drying tower to allow growth by wetting with a freshly sprayed in composition, or into an upper part of a fluid bed to allow growth of these particles by agglomeration. When the desired size is reached, the particles are removed. At least 90% by weight of the particles removed are in the range of 100–400 $\mu$m and have a water content of 0.5–4% by weight.

The particles may be incorporated into food, beverage, pharmaceutical, and/or feed products. When the active ingredient is a flavor, it may be a single ingredient, a compounded flavor, a process flavor, an essential oil such as lime, lemon, orange, peppermint, cinnamon, pepper, and/or ginger, and/or an extract.

The invention is also directed to a dust-free powder of microcapsules containing at least one active ingredient. At least 90% by weight of the microcapsules have a particle size of about 100–400 $\mu$m, a bulk density of at least 0.4 g/ml and a moisture content of 0.5–4% by weight. The microcapsules are produced by method previously described.

The invention is also directed to a method for flavoring a product by adding microcapsules containing at least one flavor and prepared as previously described. Flavor microcapsules may be added to dry food products such as instant soups, sauces, or desserts, dry beverage products such as tea or coffee, or confectionery products.

DETAILED DESCRIPTION

The new process is able to cost effectively produce microcapsules containing one or more active ingredients in a glassy matrix. The microcapsules are in the range of 100–400 $\mu$m, permit low hygroscopicity and are oxidation stable, i.e. addition of antioxidants is not necessary. In the case of liquid and/or volatile ingredients, especially in case of liquid and/or volatile flavors, at least 85% of their load at the beginning of the process should be retained in the microcapsules. Further, the powder of the microcapsules should be free flowing, non-dusting, and easily dissolvable or distributable in a food, feed or beverage, i.e. easy to use. Although the following description is related directly to flavors, it is clear to a person of skill in the art that it is also valid for other active ingredients. Thus, the invention is not restricted to flavors only, but incorporates all active ingredients such as food, feed, beverages or pharmaceutical additives.

Surprisingly, it has been found that the drawbacks of the prior art spray drying methods for encapsulation in glassy matrices can be reduced or eliminated by the process of the invention. The process uses a multi-stage spray drying unit characterized by the following steps:

a) forming an aqueous solution which contains, on a solid basis, from 40–70% by weight of at least one low molecular weight carbohydrate and/or polyhydroxy compound, and 30–60% by weight of at least one high molecular weight film forming agent, whereby the aqueous solution contains at least 50% by weight of said agent(s);

b) incorporating at least one active ingredient into the solution of step a) and building an emulsion or suspension, whereby said emulsion or suspension contains, on a non-aqueous basis, between 1–35% by weight of the active ingredient(s);

c) spray drying the emulsion or suspension of step b) into a spray drying tower at an air inlet temperature of 100–180° C. and an air outlet temperature of 60–95° C.;

d) transferring to a fluid bed section the resulting surface dried semi-solid microparticles of step c) having a water content of about 10–20% by weight and having a particle size of about 10–200 $\mu$m, and continuing drying and simultaneously agglomerating said microparticles at an air temperature of between 25–55° C., especially at about 40–50° C., resulting in solid, free-flowing particles with a glassy matrix having mainly a size of 400 $\mu$m or lower and having a water content of about 2–6% by weight; and e) collecting the particles of step d), at least 90% by weight of the particles having a size in the range of 100–400 $\mu$m and a water content of 0.5–4% by weight, and (simultaneously) recycling the particles having a size mainly below about 100 $\mu$m (fines) from the fluid bed either into the spray dying tower to allow growth of these particles by wetting the particles with freshly sprayed-in emulsion or suspension of step b), or to the upper part of the fluid bed to allow growth of these particles by agglomeration to a size in the range of 100–400 $\mu$m.

The active ingredient may be a flavor, fragrance and/or vitamin for a food, feed, beverage or pharmaceutical product. Preferably the flavor is selected from the group consisting of a single flavor ingredient, compounded flavor, process flavor, essential oil or extract, whereby the essential oil especially is selected from the group consisting of lime oil, lemon oil, orange oil, peppermint oil, cinnamon, pepper, ginger and mixtures thereof.

The present invention specifically provides a process for the production of flavors encapsulated in a glassy matrix in the form of free-flowing, dust-free powder of microcapsules, at least 90% by weight, having a size of about 100–400 μm. These microcapsules have properties which exceed the advantages provided by the extruded flavors, which are regarded as the best prior art product, but that can be produced in a continuous process cycle and with higher flavor loads, thus resulting in significantly lower production costs and costs in use.

The invention produces free-flowing, glassy matrix encapsulated flavors at lower product exposure temperatures than during standard spray drying. This improves flavor retention, reduces thermal decomposition of sensitive flavors and, further, enhances shelf life stability by reducing the matrix porosity resulting from expansion and ballooning that take place at high drying rates.

In addition, the inventive process needs no prolonged drying times and coatings as, for example, described in the above cited publication WO 91/17821, keeping production costs low.

Further, the inventive process produces free-flowing glassy particles of low hygroscopicity. This occurs by reducing the sugar content of the matrix without the need to increase the temperature during the encapsulation process as required with extrusion processes.

Further details and advantages of the inventive process are described.

The inventive process also encapsulates volatile flavors and/or other active ingredients in a glassy matrix to provide a dense, free flowing powder of 100–400 μm particle size that contains a high level of the volatile encapsulant.

Generally, the process of the invention comprises the steps of (1) preparing an aqueous solution of the matrix materials, (2) mixing the flavor into the aqueous solution with stirring to form an emulsion or suspension, (3) spraying the emulsion in a spray drying tower under a supply of hot air to quickly create a semi-solid skin allowing out take of moisture (water), and (4) subsequently subjecting the resulting particles to continued drying at lower temperatures in a fluid bed.

The matrix materials consist of low molecular weight water-soluble molecules, and at least one high molecular weight film forming agent. The low molecular weight water-soluble molecules are mono-, di- and oligosaccharides, especially glucose, fructose, maltose, sucrose, lactose, maltodextrin and inulin, or polyhydroxy compounds, especially xylitol, mannitol, sorbitol, lactitol, maltitol and isomalt. The film forming agent material is preferably protein, gum acacia, pectin, modified starch (such as, for example, Capsule E® (octenyl succinated starch, National Starch), a polyglycerol fatty acid ester, or a mixture thereof.

If the active ingredient is a water-insoluble liquid, especially a flavor oil, in order to build an emulsion or suspension, the active ingredient is preferably added to the aqueous solution of matrix materials. The mixture is then homogenized until its droplet/particle size is between about 0.2 and 10 μm, preferably about 1–2 μm, whereby the emulsion or suspension is preferably adjusted to a viscosity of about 400–1000 cP at 40° C. The amount of the active ingredient, especially the flavor oil, in the emulsion or suspension is, on a non-aqueous basis, from about 1–30% by weight, preferably from 5 to 25%, more preferably from 10–20%.

In an embodiment of the process of the invention, the liquid drops are specifically dried in two steps.

In the first step the emulsion, which is preferably heated to between 30–50° C., is sprayed into the spray drying tower in the form of fine drops built by means of a rotating disc or a nozzle, where they meet a stream of air at a temperature of between 130–180° C., more specifically at a temperature of between 145–165° C. As a result, the matrix material in the outer part of the drops solidifies, forming particles with a skin that is still permeable for water but no longer permeable for flavorants. The temperature of the hot air is kept high enough so that migration of moisture from the inside to the outside may take place within a short time, but kept low enough to prevent an explosion of steam in the droplets. Otherwise, explosion of steam would increase porosity, and hence make the matrix also permeable to flavors and oxygen, yielding flavor loss, either as liquid or by volatilization and/or oxidation of the flavors. Therefore, the temperature at the outlet of the spray dryer is normally kept at 95° C. or below 95° C., specifically in the range of 60–95° C.

In the second step of the process, the powder is fluidized in the internal fluid bed where some agglomeration takes place, which is supported by the residual moisture in the particles, which softens the surface when migrating from the inside to the outside of the particles. Residence time in the internal fluid bed is normally about 10 to 30 minutes and depends on the size of the envisaged particle size distribution of the end product. Incoming air at a temperature from 25–60° C., specifically at a temperature of about 40–50° C., passing through the fluid bed, further dries the particles. Those particles having the envisaged size are separated or collected, e.g. sieved off, and the fines are recirculated. Thus, particles are continuously dried and removed. The separated particles have a bulk density of at least 0.4 g/ml and a moisture content of 0.5–4% by weight.

The fine particles, mainly below about 100 μm (fines), are preferably collected by cyclones or in filters. They are returned into the spray dryer tower or, alternatively, to the upper part of the fluid bed where they are agglomerated with the other particles, thereby enhancing size to a size in the envisaged range of 100–400 μm. In this way a dust free powder is obtained.

A method for flavoring a food or beverage product or feed supplement may advantageously be performed by adding the encapsulated flavor in form of microparticles prepared by the inventive process in an effective amount. The microparticles may be compressed to build bigger units, and may be compressed into tablets, which in some applications might have an advantage in handling. Preferably the food in this respect is a dry mix of food, especially an instant soup, sauce or dessert or confectionery, and the beverage product preferably is a dry beverage product, especially a dry beverage powder. More preferably, the dry beverage product is a tea or instant coffee.

The present invention is described further in the following examples which are presented solely for the non-limiting purpose of further illustrating the invention.

EXAMPLE 1

An emulsion was prepared from the ingredients listed below:

| Ingredient | Quantity (kg) |
| --- | --- |
| Water | 78.49 |
| Potassium hydroxide | 0.04 |
| N-Lok | 24.91 |
| Maltodextrin | 46.74 |
| Santone 8-1-0 (polyglycerol oleic acid ester) | 2.13 |

| Ingredient | Quantity (kg) |
| --- | --- |
| Sucrose | 71.94 |
| Lemon oil | 25.75 |
| Total: | 250.00 |

Water, contained in a jacketed tank, was heated to 50–60° C. and potassium hydroxide was added with stirring using a high shear mixer. The other ingredients were then added, one after the other, with addition of the next ingredient not started until the last one had completely dissolved. Finally, the lemon oil (flavor oil) was added and the mixture was homogenized until the oil droplet size was between 5 and 10 µm. The emulsion temperature was kept at 30–40° C. while spray drying. The feed was pumped through a high-pressure homogenizer set at 150 bar in order to further reduce the size of the flavor droplets to about 1 to 2 µm. The emulsion was fed to a pressure nozzle installed on a multistage spray dryer (Anhydro SPD) and sprayed into the spraying tower under the conditions specified below.

| | |
| --- | --- |
| Total solids (kg) | 171.5 |
| Total solids [%] | 63.8 |
| Inlet spray [° C.] | 130–150 |
| Outlet spray [° C.] | 70 |
| Inlet internal fluid bed [°C.] | 40 |
| Inlet external fluid bed [°C.] | 35 / 25 |
| Spray pressure [bar] | 130 |
| Nozzle (type, diameter) | 27/1; 660 µm |
| Time [hrs] | 2.15 |
| Powder yield [kg] size: 100–400 µm | 166.2 |
| Powder yield [%] size: 100–400 µm | 97 |

The fines from the cyclone were recycled into the internal fluid bed. Thus a free flowing powder was obtained with the following properties:

Mean particle size (D(v,0.5)): 212 µm

Moisture content: 2.5%

Tap bulk density: 0.71 g/ml

Absolute density as determined by air pycnometer: 1.2817 g/ml

Total flavor content: 13.5%

Surface oil: <0.1%

EXAMPLE 2

An emulsion was prepared from the ingredients listed below:

| Ingredient | Quantity (kg) |
| --- | --- |
| Water | 95.00 |
| Capsul | 15.81 |
| Maltodextrin | 39.52 |
| Sucrose | 76.42 |
| Orange Flavor 74379 | 23.25 |
| Total: | 250.00 |

The emulsion was prepared as described in example 1. Water was heated to 50–60° C. and the solid ingredients were dissolved, one after the other. After adding the orange flavor an emulsion was prepared and dried on the multistage spray dryer. The emulsion temperature was kept at 45–50° C. while spray drying. The details of the experiment are listed below.

| | |
| --- | --- |
| Total solids [kg] | 155.0 |
| Total solids [%] | 62.0 |
| Inlet spray [° C.] | 145–165 |
| Outlet spray [° C.] | 70–73 |
| Inlet internal fluid bed [° C.] | 55 |
| Inlet external fluid bed [° C.] | 40 / 25 |
| Spray pressure [bar] | 100–115 |
| Nozzle | 27/1; 670 µm |
| Time [hrs] | 2.33 |
| Powder yield [kg] size: 100–400 µm | 147 |
| Powder yield [%] size: 100–400 µm | 95 |

A free flowing powder was obtained with the following properties:

Mean particle size (D(v,0.5)): 142 µm

Moisture content: 3.8%

Tap bulk density: 0.65 g/ml

Absolute density as determined by air pycnometer: 1.2390 g/ml

Total flavor content: 14.0%

Surface oil: <0.1%

The products of both examples were free flowing and non-dusting powders consisting of particles having a high active ingredient content. The particles had a size double that produced according to normal tower dryer techniques, but yet a size which makes it easy for particle dissolution or distribution in the food, feed, beverage or pharmaceutical end product. The flavor oil recovery was high, namely 88–95%, whereby the so-called surface oil, i.e. the flavor oil persisting on the surface of the particles, was extremely low. The particles had high densities, which is indicative of low porosities of the particles. Further, the oxygen uptake in meq/kg flavor oil in encapsulation was very low, indicating excellent encapsulation protection from oxygen attack and also from friability.

The shelf life was about 24 to 36 months. Thus, based on the above analytical results and the specific configuration of the microparticles, the shelf life was enhanced tremendously compared with encapsulated flavor particles prepared according to present methods. The particles yielded extremely good flavor stability and, hence, significantly longer shelf life. This is not known so far for similar products.

While the invention has been illustrated and described with respect to illustrative embodiments and modes of practice, it will be apparent to those skilled in the art that various modifications and improvements may be made without departing from the scope and spirit of the invention. Accordingly, the invention is not to be limited by the illustrative embodiments and modes of practice.

What is claimed is:

1. A method for encapsulating an active ingredient in a matrix to form a free flowing particle that is dust free during handling, the method comprising
   (a) partly drying in a spray drying tower a composition selected from the group consisting of a suspension and an emulsion of said ingredient and an aqueous solution of said matrix material at an air temperature of about 100–180° C. to form partly dried particles of said ingredient in said matrix material having a semi-solid skin, and (b) transferring the partly dried particles for further drying and agglomerating at an air temperature between 25–60° C. to produce said free-flowing particles.

2. A dust-free powder of microcapsules comprising at least one active ingredient in a matrix material produced by (a) partly drying in a spray drying tower under a supply of air at a temperature of about 100–180° C. a composition selected from the group consisting of (i) a suspension and (ii) an emulsion of said ingredient, and an aqueous solution of said matrix material to form particles, and (b) transferring the partly dried particles to a fluid bed dryer at a temperature of between 25–60° C. for further drying and simultaneously agglomerating said particles to produce free-flowing particles.

3. A method for flavoring a product comprising adding to said product an effective amount of a plurality of microcapsules of at least one flavor in a matrix, said microcapsules prepared by (a) spray drying a composition selected from the group consisting of a suspension and an emulsion of said flavor and an aqueous solution of said matrix to form particles by partly drying under a supply of air at a temperature of about 100–180° C., and (b) transferring the partly dried particles to a fluid bed dryer at a temperature of between 25–60° C. for further drying and simultaneously agglomerating said particles to produce said free flowing particles.

4. The method of claim 1 wherein said further drying is in a fluid bed dryer.

5. The method of claim 1 wherein said further drying is in a moving belt dryer.

6. The method of claim 1 wherein said drying in (a) is in a spray drying tower having an air inlet temperature in the range of 100–180° C. and an air outlet temperature in the range of 60–95° C.

7. The method of claim 1 wherein said drying in (a) is in a spray drying tower having an air inlet temperature of about 130–180° C.

8. The method of claim 1 wherein said drying in a) is in a spray drying tower having an air inlet temperature of about 145–160° C.

9. The method of claim 1 wherein said matrix comprises at least one low molecular weight water soluble molecule and at least one high molecular weight film forming agent.

10. The method of claim 9 wherein said low molecular weight water soluble molecule is a carbohydrate selected from the group consisting of a monosaccharide, a disaccharide, an oligosaccharide, a corresponding polyhydroxy compound, and combinations thereof.

11. The method of claim 10 wherein the carbohydrate is selected from the group consisting of glucose, fructose, maltose, sucrose, lactose, maltodextrin and inulin.

12. The method of claim 10 wherein the polyhydroxy compound is selected from the group consisting of xylitol, mannitol, sorbitol, lactitol, maltitol and isomalt.

13. The method of claim 9 wherein said film forming material is selected from the group consisting of protein, gum acacia, pectin, modified starch, a polyglycerol fatty acid ester, and combinations thereof.

14. The method of claim 1 wherein said active ingredient in said composition is in an amount of from about 1–30% by weight on a non-aqueous basis.

15. The method of claim 1 wherein said composition is first heated to a temperature in the range of 30–50° C. and drops of said heated composition are sprayed into a drying tower in a stream of air at a temperature in the range of 130–180° C. to form particles having a water-permeable matrix.

16. The method of claim 15 wherein said drops are produced by passage of said heated composition through a rotating disc or nozzle.

17. The method of claim 1 wherein said further drying comprises transferring said particles having a water content of about 10–20% by weight and a particle size of about 10–200 $\mu$m and continuing said drying and agglomerating said particles at an air temperature of between 25–60° C. to produce microparticles having a size of at most 400 $\mu$m and a water content of about 2–6% by weight.

18. The method of claim 17, wherein said air temperature is between 40–50° C.

19. The method of claim 1 further comprising recycling the further dried particles from-(b) having a size below about 100 $\mu$m from the fluid bed dryer into an upper part of a fluid bed to allow growth of these particles by agglomeration to a size in the range of 100–400 $\mu$m and thereafter removing said particles.

20. The method of claim 17 wherein at least 90% by weight of said removed particles have a size in the range of 100–400 $\mu$m and a water content of 0.5–4% by weight.

21. The method of claim 1 wherein said active ingredient is selected from the group consisting of a flavor, a fragrance, a vitamin and combinations thereof.

22. The method of claim 1 further comprising incorporating said microparticles into a product selected from the group consisting of a food, a feed, a beverage, a pharmaceutical, and combinations thereof.

23. The method of claim 21 wherein the flavor is selected from the group consisting of a single ingredient, a compounded flavor, a process flavor, an essential oil, an extract, and combinations thereof.

24. The method of claim 23 wherein the essential oil is selected from the group consisting of lime oil, lemon oil, orange oil, peppermint oil, cinnamon, pepper, ginger and combinations thereof.

25. The method of claim 1 wherein said aqueous solution contains on solid basis from 40–70% by weight of said at least one low molecular weight molecule and 30–60% by weight of said at least one high molecular weight film forming agent.

26. The method of claim 25 wherein said aqueous solution contains at least 50% by weight of said agent.

27. The method of claim 1 wherein said composition contains on aqueous basis between 1–35% by weight of said active ingredient.

28. The microcapsules of claim 2 wherein the particles are partly dried at a temperature of 130–180° C.

29. The microcapsules of claim 2 wherein the particles are partly dried at a temperature of 145–165° C.

30. The microcapsules of claim 2 wherein the particles are further dried at a temperature of about 40–50° C.

31. The microcapsules of claim 2 having heat, moisture and oxygen stability.

32. The method of claim 3 wherein the microcapsules are compressed into tablets.

33. The method of claim 3 wherein the microcapsules are added to product selected from the group consisting of a food product, a feed supplement, a beverage product, a pharmaceutical product, and combinations thereof.

34. The method of claim 3 comprising adding the encapsulated flavor to a dry mix of food.

35. The method of claim 33 wherein said food product is selected from the group consisting of an instant soup, a sauce, a dessert, and combinations thereof.

36. The method of claim 33 wherein the beverage product is a dry beverage product.

37. The method of claim 36 wherein the dry beverage product is a powder.

38. The method of claim 36 wherein the dry beverage product is selected from the group consisting of tea and coffee.

39. The method of claim 33 wherein the food product is a confectionery.

40. A plurality of microcapsules comprising at least one active ingredient in a matrix material produced by drying in a spray drying tower under a supply of air at a temperature of about 100–180° C., transferring the partly dried particles to a fluid bed for final drying at a temperature of between 25 and 60° C. while recirculating the finer particles from the fluid bed into the spray drying tower or into the upper part of the fluid bed to allow growth of the particles by agglomeration.

* * * * *